(12) United States Patent
Hatch

(10) Patent No.: US 6,238,565 B1
(45) Date of Patent: *May 29, 2001

(54) MONOLITHIC MATRIX FOR SEPARATING BIO-ORGANIC MOLECULES

(75) Inventor: Richard Hatch, Berkeley, CA (US)

(73) Assignee: Varian, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/154,529

(22) Filed: Sep. 16, 1998

(51) Int. Cl.$^7$ .................................................. B01D 15/08
(52) U.S. Cl. ........................ 210/635; 210/656; 210/659; 210/198.2; 435/6; 536/23.1; 536/25.4
(58) Field of Search .................................. 210/635, 656, 210/659, 198.2; 435/6; 536/23.1, 25.4

(56) References Cited

U.S. PATENT DOCUMENTS

| | | | |
|---|---|---|---|
| 5,334,310 | 8/1994 | Frechet et al. | 210/656 |
| 5,453,185 | 9/1995 | Frechet et al. | 210/656 |
| 5,583,162 | * 12/1996 | Li | 521/56 |
| 5,585,236 | * 12/1996 | Bonn | 210/656 |
| 5,645,717 | 7/1997 | Hjertén et al. | 210/656 |
| 5,647,979 | 7/1997 | Liao et al. | 210/656 |
| 5,795,976 | * 8/1998 | Oefner | 536/25.4 |
| 5,929,214 | * 7/1999 | Peters | 530/417 |

FOREIGN PATENT DOCUMENTS

| | | | |
|---|---|---|---|
| WO 94/11305 | 5/1994 | (WO) | 210/198.2 |
| WO 95/34359 | 12/1995 | (WO) | 210/656 |
| WO 97/19347 | 5/1997 | (WO) | 210/158.2 |

OTHER PUBLICATIONS

Article by Liao et al., entitled "Continuous Beds for Microchromatography: Reversed–Phase Chromatography", published in *Analytical Biochemistry*, vol. 234, pp. 27–30 (1996).

Article by Giovannini et al., entitled "High–Performance Membrane Chromatography of Supercoiled Plasmid DNA", published in *Anal. Chem.*, vol. 70, pp. 3348–3354 (1998).

Article by Bio–Rad Laboratories entitled "Nucleotide and Oligonucleotide Separations on an UNO Q1 Ion Exchange Column". pp. 1–4 (Undated).

Article by Viklund et al, entitled "'Molded' Macroporous Poly (glycidlyimethacrylate–co–trimethylolpropane trimethacrylate), Materials with Fine Controlled Porous Properties: Preparation of Monoliths Using Photoinitiated Polymerization" published in *Chem Mater.* In 1997, in vol. 9, pp. 463–471.

Article by Pontén et al., entitled "Solid Phase Chemiluminescence Detection Reactors Based on in Situ Polymerized Methacrylate Materials," published in *Anal. Chem.* in 1996, in vol. 68, pp. 4389–4396.

Article by Viklund et al., entitled "Monolithic, 'Molded', Porous Materials with High Flow Characteristics for Separations, Catalysis, or Solid–Phase Chemistry: Control of Porous Properties during Polymerization," published in *Chem. Mater* in 1996, in vol. 8, pp. 744–750.

* cited by examiner

*Primary Examiner*—Ernest G. Therkorn
(74) *Attorney, Agent, or Firm*—Bella Fishman; LeAnn Gorthey (57) ABSTRACT

The present invention provides monolithic polymer matrices for the separation of bio-organic molecules by liquid chromatography. In one embodiment, the matrix is formed from a polymerization mixture including (i) a hydrophobic monomer, (ii) a crosslinking agent, and (iii) a porogenic solvent or mixture of porogenic components. The monolithic matrices of the invention are particularly useful for resolving polynucleotides (e.g., DNA and/or RNA) in samples by way of reversed-phase ion-pairing chromatography.

14 Claims, 3 Drawing Sheets

MONOLITHIC MATRIX FOR SEPARATING BIO-ORGANIC MOLECULES

FIELD OF THE INVENTION

The present invention relates to the separation of bio-organic molecules. In particular, the invention provides a monolithic polymer matrix for the separation of polynucleotides by reversed-phase ion-pairing chromatography.

BACKGROUND OF THE INVENTION

Polynucleotide separations have become increasingly important in recent years. Separating polynucleotide species contained in a sample is useful, for example, in the detection andlor quantification of DNA that is the product of amplification reactions, and in the detection of variant DNA (e.g. polymorphisms or mutations). Due in large part to the complex structures and large sizes of such molecules, however, none of the separation techniques devised to date have proven wholly satisfactory.

Traditionally, polynucleotide separations have been performed using electrophoretic methods, such as slab gel electrophoresis or, more recently, capillary electrophoresis. Generally, these methods involve passing an electric current through a medium into which a mixture containing the species of interest has been injected. Each kind of molecule travels through the medium at a different rate, depending upon its electrical charge and size. Unfortunately, the electrophoretic methods are associated with certain disadvantages. For example, slab gel electrophoresis suffers the drawbacks of relatively low speed, difficulty in detection of samples, poor quantitation, and is labor intensive. Although faster and less labor intensive, capillary electrophoresis has suffered from irreproducibility of separations due to changes in the capillary performance and relatively poor quantitation.

Liquid chromatography has provided an alternative to the electrophoretic separation methods. Generally, the liquid chromatographic methods rely on differences in partitioning behavior between a flowing mobile phase and a stationary phase to separate the components in a mixture. A column tube, or other support, holds the stationary phase and the mobile phase carries the sample through it. Sample components that partition strongly into the stationary phase spend a greater amount of time in the column and are separated from components that stay predominantly in the mobile phase and pass through the column faster. As the components elute from the column they can be quantified by a detector and/or collected for further analysis.

Typical stationary phases, and their interactions with the solutes, used in liquid chromatography are:

| NAME | STATIONARY PHASE | INTERACTION |
|---|---|---|
| Size-Exclusion | Porous inert particles | Samples are separated by virtue of their size in solution; different sized molecules will have different total transit times through the column. |
| Ion-Exchange | Ionic groups on a resin | Sample ions will exchange with ions already on the ionogenic group of the packing; retention is based on the affinity of different ions for the site and on a number of other solution parameters (pH, ionic strength, counterion type, etc.). |
| Reverse-Phase | Non-polar groups on a resin | Samples are separated based on hydrophobic interactions with the stationary phase. |

Although the liquid chromatographic methods have some advantages over electrophoretic separation techniques, they are not without their shortcomings. Size-exclusion chromatography suffers from low resolution, as, typically, DNA molecules must differ in size by 50–100% in order to obtain acceptable resolution. Although ion-exchange chromatography offers higher resolution, it can be affected by anomalous elution orders based on DNA sequence composition. Also with ion-exchange chromatography, the eluted DNA is often heavily contaminated with nonvolatile buffers that can further complicate sample recovery. Reverse-phase chromatography is capable of relatively high resolution but, unless special small-diameter particulates are used as the stationary phase, it cannot be performed at a very high speed. Silica-based particulates used in reverse-phase chromatography have suffered from low speed and instability at high pH conditions. Polymeric particulates have not been able to provide a high recovery of sample components or high separation speeds.

With particular regard to DNA separations, a technique known as reverse-phase ion-pair high performance liquid chromatography (RP-IP HPLC) has provided a limited amount of relief from some of the problems discussed above. For example, RP-IP HPLC avoids the problem of anomalous elution orders often encountered with packed beds bearing strong-anion exchangers. In RP-IP HPLC, the stationary phase typically consists of discrete particles bearing hydrophobic surface groups that are packed into a column. The eluent contains a cationic species, such as triethylammonium ion (0.1M), capable of interacting with the negatively charged phosphate groups on DNA and also with the hydrophobic surface of the particles in the column. Thus, the cationic species can be thought of as a bridging molecule between DNA and the column. As the mobile phase is made progressively more organic, e.g., with increasing concentration of acetonitrile, the DNA fragments are eluted in order of size.

Despite the advantages of RP-IP HPLC for DNA separations, the technique nevertheless suffers from problems common to all liquid chromatographic techniques wherein small particles (e.g., beads) are packed to form a bed in a column tube. For example, the production of particulate separation media can be complex and time-consuming. Once prepared, it can be difficult to pack the particles in columns in a reproducible and efficient manner. In particular, it has been difficult to pack efficient columns of small dimensions, such as columns less than 1 mm in diameter. Columns having norcclrcular cross-sections, such as polygonal cross-sections (e.g., thin-layer or rectangular), would be extremely difficult to prepare from particulate packing materials. Also, columns based on packed beads can fail due to shifting of packing material and the development of channels or voids. As an additional disadvantage, the use of small particles often leads to high column operating pressures, which necessitate column tubes, pumps, injectors and other components capable of containing fluid pressures of 3,000 psi or greater.

Current chromatographic theory predicts that, for beds of packed particles, separation efficiency will be determined by the diffusional distance for mass transfer of sample molecule to the stationary phase. This effect is easily modeled based on the known geometry of the particles used in such beds. According to such theory, maximum resolution will occur when the stationary phase has pore diameters of at least 3 times the Stokes' diameter of the molecule to be separated. This theory is based on the assumption that the molecule will be transported to the stationary phase by a diffusive process and that smaller pores would cause hindered diffusion. For DNA separations, this means that for a sample of 1,000 base pairs in size, a pore diameter of at least 1 micrometer will be needed. The need for such large pores practically eliminates the use of porous particulate materials packed in a support for the separation of DNA, as such matrices lack the required physical strength to be used at the operating pressures encountered in high performance liquid chromatography.

Nonporous particulate materials are preferred for DNA separations due to the reduction in diffusion distance compared to porous packings. For nonporous packings, the pore diameter is determined by the interstitial dimensions of the packed bed. The interstitial dimension is approximately ⅓ of the diameter of a spherical packing particle. A lower limit to the pore diameter may be imposed by the need to avoid trapping or shearing of larger DNA molecules. A higher limit will be imposed by the loss of efficiency that occurs when using larger particles. Separation using larger particles would be advantageous because of the lower operating pressures involved, but the loss in separation efficiency is too great.

As a further disadvantage, spherical packings can be packed into stable beds only at densities approximating an interstitial void fraction of about 0.4. Although somewhat more variable, nonspherical packings are also packed optimally at void fractions of about 0.4. Moreover, packed-particulate beds have fixed surface areas, fixed interstitial distances, and fixed pressure drops determined by the particle diameter of the packing material. Since DNA has a physical size approximating 0.34 micron per 1,000 base pairs of length and efficiency will be highest when the interstitial distance is 3–10 times the Stokes' diameter of the molecules being separated, a column designed for DNA of 1,000 base pairs could require an interstitial distance of 1–3 microns. Columns with packing of 3–10 micrometers in diameter would provide such distances. A column packed with 3 micrometer packings will have high operating pressures in use, whereas a column packed with 10 micrometer packings will show limited efficiency due to longer diffusional paths and lower binding capacity due to a decreased surface area. While columns packed with very small particles, such as 1 micrometer diameter, could be useful for samples up to 300 base pairs in length, column operating pressures would be very high and DNA larger than 300 base pairs could be sheared or trapped. A typical column of packed beads uses particles of 2.1 micrometers in diameter and has high operating pressure under typical use.

The above theory relating to beds of packed particles is not particularly useful for predicting the behavior of macromolecules in continuous monolithic beds, where mass transport may be a combination of diffusive and convective processes.

The present invention, which teaches monolithic beds for resolving mixtures containing polynucleotides, is based in part on the discovery that monoliths provide reduced pressure drops corresponding to the use of large particle stationary phases while maintaining the separation resolution of columns packed with small spherical particles. More particularly, it has been discovered that reversed-phase monolithic matrices can provide an improved method for the high speed separation of DNA molecules and that such separations can be performed with high resolution at greatly reduced operating pressures compared to previously available methods. This surprising finding now permits the high-resolution separation of polynucleotides under conditions not possible with preexisting technology. Moreover, the monolithic columns of the present invention can be constructed with stationary phase geometries significantly different than those available with packed beds. The effects of such novel geometries on the separation of macromolecules have not been predicted so far by current chromatographic theory.

The monolithic columns of the present invention provide all of the advantages of the previous best technology for polynucleotide separations (i.e., packed beds of alkylated nonporous polymer beads), without the need to tediously prepare beads and pack them into efficient columns. The columns produced by the current invention are easily prepared using simple processes and once prepared, cannot fail through shifting within a packed bed because there are no individual beads to shift position.

In addition to the improved ease of manufacturing of the new columns and lack of bead shifting, the monolithic columns described herein provide a surprising advantage over the existing technology in that they can offer at least 58% better resolution than that expected for a column of packed spheres when normalized for operating pressures.

SUMMARY OF THE INVENTION

One aspect of the present invention provides a method for resolving a mixture containing at least one polynucleotide (e.g., DNA and/or RNA). According to the method, the mixture is passed through a monolithic polymer matrix held in a stationary fashion by a support. The mixture is separated by ion-pair reverse-phase chromatography.

In one embodiment, the monolithic polymer matrix has hydrophobic surface groups. The monolithic polymer matrix can be comprised, at least in part, of a polymer selected from the group consisting of polymethacrylates and polystyrenes. In one embodiment, the polymer is a polymethacrylate.

According to one embodiment, the monolithic polymer matrix is formed from a polymerization mixture including a hydrophobic monomer, a crosslinking agent, and a porogen. The porogen may be (i) a porogenic solvent, (ii) a mixture of porogenic solvents, or (iii) one or more porogenic solvents containing at least one polymeric additive that contributes to pore formation. The hydrophobic monomer can be an alkyl methacrylate.

In one embodiment, the method further includes the step of passing an eluant containing an ion-pairing agent through the monolithic matrix. The separation is carried out under the driving force of a reasonable pressure (e.g., less than about 5,000 psi).

For the support, one embodiment contemplates the use of a column tube having a circular cross-section. Another embodiment contemplates the use of a column tube having a non-circular, e.g., polygonal, cross-section.

An additional embodiment contemplates the use of a plate as the support. The monolithic polymer matrix may fill a channel formed in the plate, or it may take the form of a thin film on the plate.

Still a further embodiment contemplates the use of a chip (e.g., as fabricated by techniques employed in the semiconductor arts) as the support. In this embodiment, the matrix is held in a microfabricated channel formed in the chip. In a related embodiment, a plurality of microfabricated channels are formed in the chip, and multiple separations are carried out in a substantially simultaneous fashion on the chip.

Another aspect of the invention provides a chromatographic apparatus comprising a support holding a macroporous monolithic methacrylate-based polymer matrix. In one embodiment, the polymer matrix has a hydrophobic surface capable of interacting with hydrophobic groups of an ion-pairing agent for resolving polynucleotides by reverse-phase ion-pair chromatography. The polymer matrix may have a relatively high void fraction (e.g., greater than about 0.6).

A further aspect of the invention provides kits for resolving polynucleotides by reverse-phase ion-pair chromatography.

In one embodiment, the kit includes: (i) a polymerization mixture including a monomer having hydrophobic surface groups, a crosslinking agent, and a porogen; and (ii) an ion-pairing agent capable of interacting with negatively charged phosphate groups of the polynucleotides and also with the hydrophobic surface groups of the monomer.

In another embodiment, the kit includes: (i) a monolithic polymer matrix having hydrophobic surface groups held in a stationary fashion by a support; and (ii) an ion-pairing agent capable of interacting with negatively charged phosphate groups of the polynucleotides and also with the hydrophobic surface groups of the monomer.

These and other features and advantages of the present invention will become clear from the following description.

BRIEF DESCRIPTION OF THE DRAWINGS

The structure and manner of operation of the invention, together with the further objects and advantages thereof, may best be understood by reference to the following description taken in conjunction with the accompanying drawings, in which.

DEFINITIONS

As used here, the term "polynucleotide" refers to a polymer of ribonucleic acid (RNA) or deoxyribonucleic acid (DNA), which can be single- or double-stranded, optionally incorporating synthetic, non-natural, or altered nucleotides capable of incorporation into DNA or RNA polymers, e.g., methylated nucleotides and nucleotide analogs. Polynucleotides may have any three-dimensional structure, and may optionally be partially or fully denatured. The following are non-limiting examples of polynucleotides: a gene or gene fragment (e.g., restriction fragments), exons, introns, messenger RNA, transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

The term "columns," as used herein, is intended to include devices where a fluid mobile phase is transported through a stationary bed, regardless of the physical cross-section or dimension of the bed.

The "permeability" of a column bed is a measure of the abundance of large-diameter pores.

DETAILED DESCRIPTION OF THE INVENTION

The following discussion of the preferred embodiments of the present invention is merely exemplary in nature. Accordingly, this discussion is in no way intended to limit the scope of the invention, application of the invention, or the uses of the invention.

The present invention provides a monolithic bed, and method of making and using the same, for resolving bioorganic molecules.

The columns of the invention are prepared from a polymerization mixture which, in one no embodiment, includes (1) a monomer, (2) a crosslinking agent, and (3) a porogen (e.g., a porogenic solvent or mixture of porogenic components). In this embodiment, the mixture is placed in a suitably-shaped mold, and subjected to the influence of a polymerization initiator to start a polymerization process which finally yields a macroporous polymer matrix which contains porosity such that a liquid can be passed through the matrix under the driving force of a reasonable pressure (e.g., less than about 5,000 psi).

A monomer, or combination of monomers, is chosen such that the polymerized matrix will include surface groups that can interact with polynucleotides to provide separation based on ion-pair chromatography. In one preferred embodiment, a species bearing hydrophobic surface groups is utilized as the monomer. Optionally, the monomer may be modified to exhibit the desired degree of hydrophobicity. For example, appropriate ligands may be covalently attached to the monomer, by methods known in the art, to improve its effectiveness as a medium for reverse-phase chromatography. Alternatively, or in addition, the polymerized matrix itself may be treated to attach ligands imparting the desired degree of hydrophobicity thereto. If the monomer, or combination of monomers, chosen for use in the polymerization mixture does not otherwise exhibit the desired hydrophobic characteristics, then treatment to add appropriate ligands (e.g., aliphatic surface groups) may be required in order to render the column useful for reverse-phase separations.

In one embodiment, the monomer utilized in the polymerization mixture bears at least one type of alkyl group capable of serving as a hydrophobic group for reversed-phase chromatography. Preferred alkyl groups are those having from about 3–30 carbons, and most preferably within the range of about 4 to 18 carbons. Exemplary monomers useful for practicing the invention include hexyl methacrylate, octyl methacrylate, and dodecyl methacrylate. The invention also contemplates the use of a styrene monomer.

Any suitable crosslinking agents known to those skilled in art may be employed in forming the monolithic matrix of the invention. Preferred crosslinking monomers contain at least two carbon-carbon double bonds capable of polymerization in the presence of an initiator. Exemplary crosslinking monomers include divinyl benzene, butadiene, trimethylolpropane trimethacrylate (TRIM), etc.

It should be appreciated that a single species may comprise both the monomer and the crosslinking agent For example, a hydrophobic crosslinker may serve both of these roles. In this regard, one embodiment of the present invention contemplates the use of TRIM as the only monomer in the polymerization mixture, as well as the only crosslinking agent.

The monomer, or combination of monomers, is generally present in the polymerization mixture in an amount of from about 20 to 80 vol. %, and more preferably in an amount of from about 35 to 50 vol. %.

Conventional free-radical generating polymerization initiators may be employed to initiate polymerization. Examples of suitable initiators include peroxides such as OO-t-amyl-O-(2ethylhexyl)monoperoxycarbonate, dipropylperoxydicarbonate, and benzoyl peroxide, as well as azo compounds such as azobisisobutyronitrile, 2,2'-azobis (2-amidinopropane)dihydrochloride, and 2,2'-azobis (isobutyramide)dihydrate. The initiator is generally present in the polymerization mixture in an amount of from about 0.1 to 2% by weight of the monomers.

The porogen used may be selected from a variety of different types of materials. The porogen can be (i) a single porogenic solvent, (ii) a mixture of porogenic solvents, or (iii) one or more solvents containing at least one polymeric additive that contributes to pore formation. Suitable liquid porogens include aliphatic hydrocarbons, aromatic hydrocarbons, esters, alcohols, ketones, ethers, solutions of soluble polymers, and mixtures thereof. Exemplary porogenic solvents incdude isooctane and isooctane with varying percentages of 2-octanone, toluene, or ethyl propionate. Exemplary polymeric additives that contribute to pore formation indude polymethyl methacrylate and polystyrene. The porogen is generally present in the polymerization mixture in an amount of from about 20 to 80 vol %, more preferably from about 50 to 65 vol %.

For TRIM-based polymerization mixtures, highly permeable monoliths will result, for example, from the use of pure lsooctane as a porogenic solvent. Lower permeability will result, for example, from addition of 5–20% of other solvents, such as 2-octanone, toluene, and/or ethyl proprionate, to the isooctane. Permeability may also be reduced by increasing the ratio of hydrophobic monomer to crosslinker, and by decreasing the proportion of porogenic solvent in the mixture. Additionally, the choice of initiator may be used as a means to control the pore distribution.

In an exemplary embodiment, the monolithic matrix is prepared from a polymerization mixture including an alkyl methacrylate, an alkane porogenic solvent or mixture of porogenic components, and a free radical initiator. For example, a polymerization mixture was prepared using trimethylolpropane trimethacrylate, an alkyl methacrylate, isooctane, and azobisisobutyronitrile. The mixture was poured into an empty HPLC column tube, capped, and polymerized at 65–70° C. for 8–24 hours. The polymerized matrix was then equipped with endfittings and flushed with solvent to remove unreacted components.

A typical monolithic column constructed in accordance with the present invention will have pores in the less than 5,000 nm range, down to about 10 nm. The size of larger pores can be determined using very large DNA andlor microscopic exam. For example, the columns of the invention have been used to separate DNA products of 2,072, 2,647, and 3,147 base pairs in length. The largest of these would correspond to a molecular size of at lease 1 micron. Accordingly, the monolithic column used to separate this DNA would be expected to include pores having a diameter of at least 1 micron. This is in agreement with permeability calculations that indicate an apparent particle diameter of 6 microns, or a pore size of about 2 microns. Microscopic exam revealed that a typical matrix of the invention includes small globules of about 1–2 microns in diameter that are fused into continuous structures with pores in the 1–5 micron size range. This is consistent with the estimated pore size based on permeability and DNA fragment chromatography.

Columns of the present invention have also been used to separate DNA down to about 17 base pairs. A relatively small DNA of 100 base pairs in length would have a size of only 34 nm. So, the high resolution made possible by the present invention is preserved for columns with pores up to at least about 170 times the length of the DNA molecules to be separated. Without committing to any particular theory, it may be this unusual feature that accounts for the low operating pressures possible with the columns of the invention.

Once prepared, the monolithic matrix of the Invention Is useful for resolving bio-organic molecules, for example, by gradient or isocratic liquid chromatography. In an exemplary use, a column of the invention, prepared as described above, is employed to carry out a separation of polynucleotides contained in a sample. In one embodiment, water and acetonitrile, both containing an ion-pairing agent, are used in gradient liquid chromatography to elute polynucleotides injected into the column.

Conventional ion-pairing agents capable of forming ion pairs with nudeic adds may be used in the present invention. Ion-pairing agents, suitable for practicing the present invention, include cationic hydrophobic species such as alkylammonium salts of organic or inorganic acids, for example tetramethyl, tetraethyl, tetrapropyl and tetrabutyl ammonium acetates, halides, etc. Dimethylbutylammonium, dimethylhexylammonium, dimethylcyclohexylammonium and diisopropylammonium acetates, among others, are effective ion-pairing agents. TEM (triethylammonium acetate) was found to be an effective ion-pairing agent in both methacrylate and styrene-based columns. Tetrabutylammonium bromide was found to be an effective ion-pairing agent for the separation of DNA fragments of length up to at least 1,000 base pairs.

A variety of support structures may be used with the monolithic matrix of the invention. For example, one embodiment contemplates the use of an elongated column tube. In another embodiment, the monolithic matrix is held in the lumen of a capillary tube. In these embodiments, the matrix extends across the entire cross-sectional area of the tube. The tube may be of any desired cross-section, e.g., circular, polygonal, or other shape. The monolithic matrix may be polymerized in situ within the tube, or it may be formed outside of the tube and then inserted by any suitable means.

In alternative embodiments, the monolithic matrix is (i) held in a channel or groove on a plate, or (ii) applied as a thin film across a plate. While the monoliths of the invention may be provided on a substrate or supporting plate of virtually any size and composed of any suitable material, one embodiment of the present invention contemplates using a supporting plate of a standard size, which can be constructed using conventional materials and means. Thus, in this embodiment, an injection molded rectangular plastic plate, the length and width of which conform to the commonly used standard of 5.030"×3.365" (127.76 mm and 85.47 mm), is preferred. Similarly, while a single plate may support any reasonable number of sites, constructions corresponding to the commonly used "96-well" microtiter plate format are preferred. Thus, one preferred construction includes an 8×12 array of sites situated on a standard-sized support plate. Each site may support one or more separate monoliths. The position and spacing of the sites on the support plate may be standard, as well (e.g., spaced about 9 mm center-to-center). Utilization of standard outside dimensions for the plate frame, as well as standard spacing for the sites on the plate, facilitates use of the plates with existing equipment, such as automated dispensers or optical readers, if desired. It should be appreciated that such an apparatus is capable of handling multiple simultaneous and parallel separations.

In a further embodiment, the monolithic matrix fills one or more channels formed on a microchip. For example, a plurality of channels can be formed on a glass microchip substrate using standard microfabrication techniques, e.g., photolithographic procedures and chemical wet etching. Optionally, a cover plate can be direct bonded to the substrate over the channels. A plurality of separations can be conducted on multiple samples in a substantially parallel fashion upon a single substrate chip.

Advantageously, the columns of this invention are not limited to the fixed surface areas, pressure drops and interstitial diffusional distances of a packed bed. Because the void fraction can be much higher in the monolithic columns taught herein, all of these factors can be manipulated for improved performance for a given application. For example, columns can be produced with the same void fraction and widely different pressure drops, or columns could be produced with the same pressure drop but different interstitial distances. In a particular example, some columns produced in this invention performing well for DNA separations have void fractions of about 0.7. A void fraction of 0.7 cannot be produced for nonporous packings by packing discrete particles.

EXAMPLES

The Examples are intended to illustrate, but not limit, the scope of the invention.

Example 1

Segaratlon of Single-Stranded Oligonucleotides

A mixture containing 1.0 ml trimethylolpropane trimethacrylate, 0.32 ml hexyl methacrylate, 2.4 ml isooctane, and about 20 mg azobisisobutyronitrile was prepared and injected into empty 4.6 mm ID×5 cm long HPLC column tubes closed at one end with an endfitting and plug. The filed tube was dosed at the other end with an endfitting and plug, then immersed in a water bath at 65° C. overnight. After reaction, the plugs and endfittings were removed and endfittings with polyethylene frits attached. The complete column was flushed with tetrahydrofuran.

Figure 1:
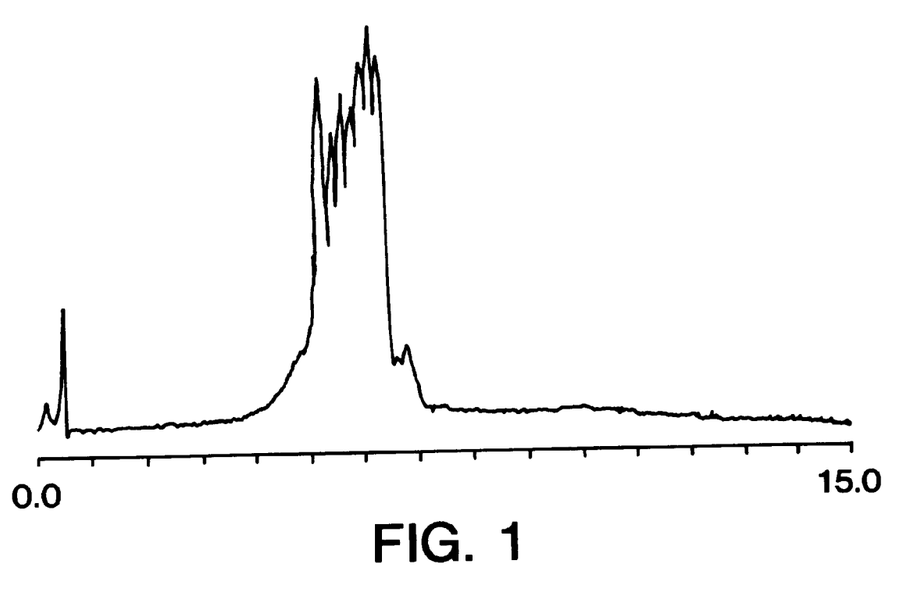
FIG. 1 is a chromatogram showing the separation of oligothymidylic acids between 12 to 18 units in length on a C6 monolithic column constructed in accordance with an embodiment of the present invention.

FIG. 1 is a chromatogram showing the separation of single-stranded oligothymidylic acids on a C6 monolithic column constructed in the manner just described. Specifically, the sample was 10 microliters of oligothymidylic adds between 12 and 18 units in length. At a flow rate of 2 ml/minute, a gradient of 0–12% acetonitrile in 100 mM aqueous triethylammonium acetate, 10 mM disodium EDTA, pH 7.0 was used to elute the oligonucleotides. Detection was performed using UV absorbance at 254 nm. An extremely low HPLC system pressure of only 150 psi was observed during the separation.

Example 2

Separation of Double-Stranded DNA

A mixture containing 1.25 ml trimethylolpropane trimethacrylate, 0.30 ml lauryl methacrylate, 2.6 ml of a mixture of 95% isooctane and 5% toluene and 17 mg azobisisobutyrontrile was prepared and injected into empty 4.6 mm ID×5 cm long HPLC column tubes closed at one end with an endfitting and plug. The filled tube was closed at the other end with an endfiting and plug, then immersed in a water bath at 65° C. overnight. After reaction, the plugs and endfittings were removed and endfitings with polyethylene ffits attached. The complete column was flushed with tetrahydrofuran.

Figure 2A:
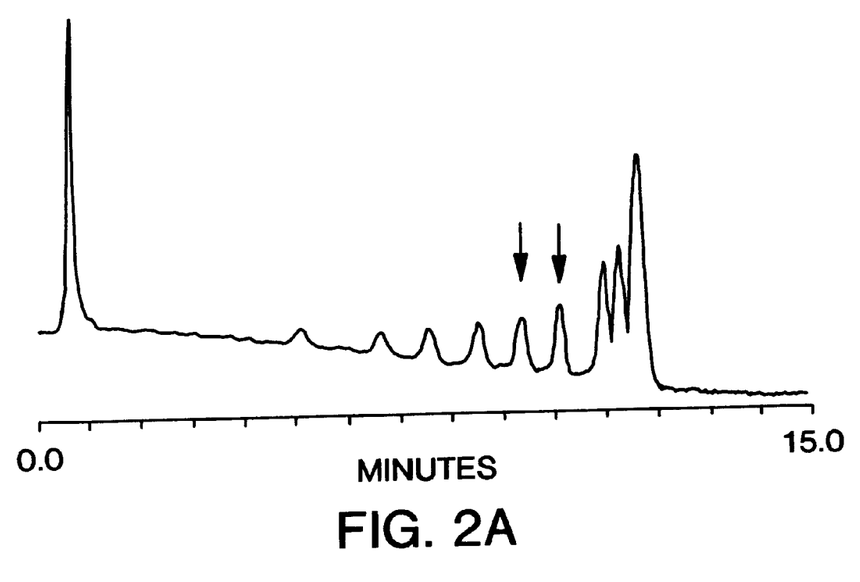
FIG. 2A is a chromatogram showing the separation of double-stranded DNA fragments on a C12 monolithic column constructed in accordance with an embodiment of the present invention.

FIG. 2A is a chromatogram showing the separation of double-stranded DNA fragments on a monolithic C12 column constructed in the manner just described. Specifically, the sample was 3 microliters of pUC18 DNA digested by the MSP I restriction enzyme. At a flow rate of 1.0 ml/minute, a 10 minute gradient of 35%–60% acetonitrile containing 2 mM tetrapropylammonium bromide in 20 mM aqueous tetrapropylammonium bromide, 2 mM disodium EDTA, pH 7.0 was used to elute the DNA fragments. Detection was performed using UV absorbance at 254 nm. At 0.5 ml/min an HPLC system pressure of 50 psi was observed. Resolution was calculated for the peaks indicated in FIG. 2A by arrows.

Figure 2B:
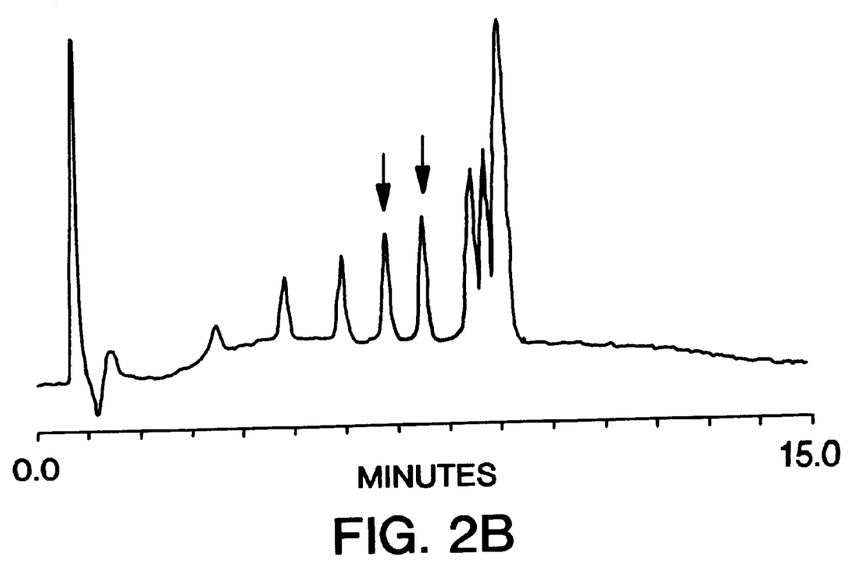
FIG. 2B is a chromatogram showing results, for comparative purposes, of a separation of double-stranded DNA fragments like those of FIG. 2A carried out on a column packed with 2.1 micrometer nonporous beads.

For comparative purposes, a similar separation was carried out using a column packed with nonporous polymer spheres. In this regard, FIG. 2B is a chromatogram showing the separation of double-stranded DNA fragments on a column packed with 2.1 μm diameter nonporous beads. In this comparative experiment, the sample was 3 microliters of pUC18 DNA digested by the MSP I restriction enzyme. At a flow rate of 0.5 ml/minute, a 10 minute gradient of 8.75%–15% acetonitrile in 100 mM aqueous triethylammonium acetate, 10 mM disodium EDTA, pH 7.0 was used to elute the DNA fragments. Detection was performed using UV absorbance at 254 nm. At 0.5 ml/min an HPLC system pressure of 1340 psi was observed. Resolution was calculated for the peaks indicated in FIG. 2B by arrows.

The chromatographic data from the above experiments are summarized in Table 1. The resolution of the marked peaks was found to be 4.04 for the monolithic column of FIG. 2A and 5.83 for the column packed with nonporous spheres in FIG. 2B. Using standard permeability calculations (Introduction to Modem Liquid Chromatography, $2^{nd}$ edition, L. R. Snyder and J. J. Kirkland, John Wiley and Sons, New York, 1979, p. 37), it can be calculated that the column of FIG. 2A has an operating pressure equivalent to that of a column packed with 6.22 micron diameter spheres whereas that in FIG. 2B would be estimated as 1.20 micron. Based on these different effective partide sizes, the column of FIG. 2A has a resolution 58% greater than expected. A critical figure of merit for chromatographic separations is the efficiency or resolution per unit pressure. It can be seen from the data of Table 1 that the monolithic column offers an order of magnitude increase in resolution per unit pressure compared to the column packed with nonporous spheres.

TABLE 1

|  | Column with Nonporous Spherical Packing | Column with C12 Monolithic Polymer |
|---|---|---|
| Retention Time Peak 1 (min.) | 6.80 | 9.36 |
| Area Peak 1 ($\mu$V*sec) | 80678.00 | 84592.00 |
| Height Peak 1 ($\mu$V) | 11370.00 | 7438.00 |
| Retention Time Peak 2 (min.) | 7.52 | 10.10 |
| Area Peak 2 ($\mu$V*sec) | 103115.00 | 103644.00 |
| Height Peak 2 ($\mu$V) | 13348.00 | 9779.00 |
| Resolution | 5.83 | 4.04 |
| Column Pressure (psi) | 1340.00 | 100.00 |
| Apparent Particle Size ($\mu$m) | 1.20 | 6.20 |
| Expected Resolution | 5.83 | 2.57 |
| Excess Resolution % | 0.00 | 58.00 |
| Resolution/1,000 psi | 4.35 | 40.42 |

Example 3

Segaration of Partially Denatured Double-Stranded Polynucleotides

Figure 3A:
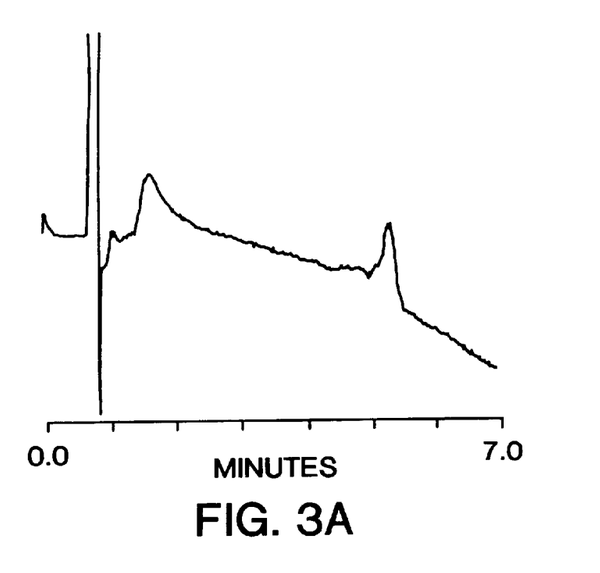
FIG. 3A is a chromatogram showing the separation of homoduplex DNA fragments 304 base pairs in length on a porous monolithic C12 column constructed in accordance with an embodiment of the present invention.
Figure 3B:
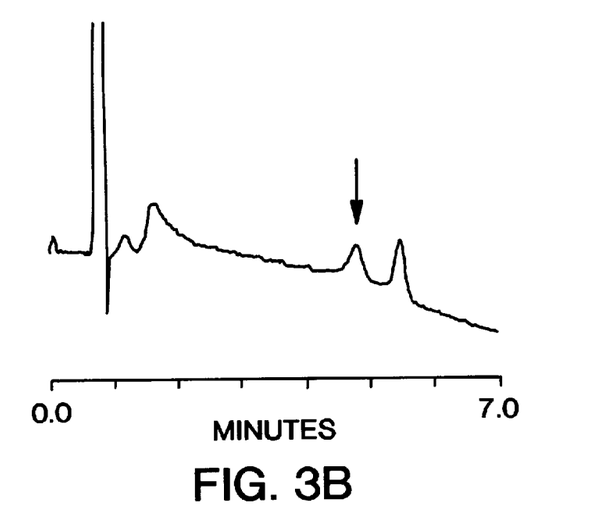
FIG. 3B is a chromatogram showing the separation of a mixture containing the same type of homoduplex DNA fragments of FIG. 3A as well as a variant sequence containing a single base pair substitution on a porous monolithic C12 column constructed in accordance with an embodiment of the present invention.

The present invention also makes possible the separation of partially denatured double-stranded polynucleotides. As shown in FIGS. 3A and 3B, a porous monolithic column was used to separate DNA fragments 304 base pairs in length. In FIG. 3A, the sample contained a single type of DNA, whereas in FIG. 3B the sample contained a mixture of the type seen in FIG. 3A and a variant sequence containing a single base pair substitution. At the selected temperature, the sample of FIG. 3B shows a second peak that represents partially denatured DNA containing the single base pair substitution.

Specifically, with regard to FIG. 3A, homoduplex DNA with sequence 304 base pairs in length was separated on a monolithic C12 column, prepared as described above. In carrying out the separation, the conditions as set out in Table 2, below, were observed:

TABLE 2

| Mobile Phase: | A: 20 mM tetrapropylammonium bromide + 2 mM disodium EDTA in water, pH 7.0 |
|---|---|
|  | B: 20 mM tetrapropylammonium bromide in acetonitrile |
| Gradient: | 50–65% B in A over 7 minutes |
| Flow Rate: | 0.75 ml/min |
| Separation temperature: | 43° C. |
| Detection: | UV, 254 nm |

Similar conditions were observed in obtaining the data of FIG. 3B, except that the sample contained, in addition to the 304 base pair homoduplex DNA of FIG. 3A, a variant heteroduplex DNA species having a single base pair substitution. The peak marked with the arrow in FIG. 3B indicates the presence of this variant DNA.

Comparative Example A

U.S. Pat. No. 5,334,310 to Frechet et al. suggests that one solution to some of the aforementioned problems associated with column beds of packed particulate materials would be the use of a continuous bed for the separation of large molecules. However, the '310 patent offers no particulars or guidance to enable the selection of a suitable matrix for the separation of DNA by the most advantageous method, RP-IP HPLC.

For comparative purposes, columns were constructed in accordance with Examples III and VI of the '310 patent. Briefly, these examples describe monolithic columns which are hydrophobic in nature. After the polymerizations of these compositions, end fittings were attached and the columns flushed with methanol, as described in the '310 patent. The composition produced by Example III of the '310 patent was translucent in appearance and had a very high operating pressure (greater than 2,000 psi at 0.25 ml/min with methanol), precluding its use in practical HPLC of DNA. The composition produced by Example VI of the '310 patent was white and had a relatively low operating pressure. However, this latter column did not provide useful separations of DNA restriction fragments under reversed-phase ion-pairing conditions. No typical pattern of peaks was observed when a separation was attempted under conditions that would provide a useful separation using the matrices of the present invention. These findings are in accord with previous suggestions in the literature that columns with unmodified polystyrene/divinylbenzene structures are not desirable for DNA separations.

Those skilled in the art can now appreciate from the foregoing description that the broad teachings of the present invention can be implemented in a variety of forms. Therefore, while this invention has been described in connection with particular embodiments and examples thereof, the true scope of the invention should not be so limited. Various changes and modification may be made without departing from the scope of the invention, as defined by the appended claims.

It is claimed:

1. A method for resolving a mixture containing at least one polynucleotide, comprising:
    applying said mixture to a porous monolithic polymer matrix held in a stationary fashion by a support,
    wherein said monolithic polymer matrix is formed from polymerization of a monomer, or combination of monomers, selected from $C_3$ to $C_{30}$ alkyl methacrylates, in the presence of a crosslinking agent and a porogenic solvent, and
    separating said mixture by ion-pair reverse-phase chromatography, by passing an eluant containing an ion-pairing agent through the monolithic matrix.

2. The method of claim 1, wherein said separating comprises passing an eluant containing an ion-pairing agent through said monolithic matrix, said ion-pairing agent being an alkylammonium salt.

3. The method of claim 1, wherein said at least one polynucleotide is selected from the group consisting of DNA and RNA.

4. The method of claim 1, further comprising the step of passing an eluant containing an ion-pairing agent through said monolithic matrix, said ion-pairing agent being capable of interacting with negatively charged phosphate groups of said at least one polynucleotide and also with said hydrophobic surface of said monolithic polymer matrix.

5. The method of claim 4, wherein the mixture is subjected to a driving force of less than about 3,000 psi.

6. The method of claim 4, wherein said support is a column tube having a circular cross-section.

7. The method of claim 4, wherein said support is a column tube having a polygonal cross-section.

8. The method of claim 4, wherein said support is a plate.

9. The method of claim 8, wherein said monolithic polymer matrix is held in a channel formed in said plate.

10. The method of claim 8, wherein said monolithic polymer matrix takes the form of a thin film on said plate.

11. The method of claim 4, wherein said support is a chip and said matrix is held in a microfabricated channel formed in said chip.

12. The method of claim 11, wherein a plurality of microfabricated channels are formed in said chip, and wherein multiple separations are carried out in a substantially simultaneous fashion on said chip.

13. The method of claim 1, wherein said solvent is selected from the group consisting of aliphatic hydrocarbons, aromatic hydrocarbons, esters, alcohols, ketones, ethers, and mixtures thereof.

14. The method of claim 13, wherein said solvent is selected from the group consisting of isooctane and a combination of isooctane with 2-octanone, toluene, or ethyl propionate.

* * * * *